United States Patent [19]

Jeffs

[11] Patent Number: 4,980,293

[45] Date of Patent: Dec. 25, 1990

[54] DISPENSING REAGENTS IN A SPECIMEN WELL

[75] Inventor: David H. Jeffs, Salt Lake City, Utah

[73] Assignee: Multi-Technology Inc., Salt Lake City, Utah

[21] Appl. No.: 240,170

[22] Filed: Sep. 2, 1988

[51] Int. Cl.[5] .................................... C12M 1/02

[52] U.S. Cl. .................................... 435/296; 435/293; 435/294; 435/300; 422/102

[58] Field of Search ............... 435/292, 293, 294, 296, 435/297, 298, 299, 300, 301, 4, 30; 422/102

[56] References Cited

U.S. PATENT DOCUMENTS

| | | | |
|---|---|---|---|
| 2,275,567 | 3/1942 | Smith | 435/300 X |
| 2,476,093 | 7/1949 | Hirsch | 422/102 X |
| 3,415,361 | 12/1968 | Adams, Jr. et al. | 435/299 X |
| 3,830,702 | 8/1974 | Beckford | 435/300 X |
| 4,065,360 | 12/1977 | Kreb, III | 435/294 |
| 4,129,483 | 12/1978 | Bochner | 435/301 X |
| 4,299,918 | 11/1981 | Popoff et al. | 435/30 |
| 4,321,330 | 3/1982 | Baker et al. | 435/284 X |
| 4,330,627 | 5/1982 | Thomas et al. | 435/293 X |
| 4,427,634 | 1/1984 | Truglio | 435/294 X |
| 4,577,760 | 3/1986 | Rainin et al. | 206/508 |
| 4,640,895 | 2/1987 | Davis | 435/292 X |
| 4,676,377 | 6/1987 | Rainin et al. | 206/508 |
| 4,770,855 | 9/1988 | Sakuma | 422/102 |
| 4,912,048 | 3/1990 | Smith et al. | 435/296 |

FOREIGN PATENT DOCUMENTS 2408109 2/1974 Fed. Rep. of Germany .

*Primary Examiner*—Robert A. Wax
*Assistant Examiner*—Janelle D. Waack
*Attorney, Agent, or Firm*—Lynn G. Foster

[57] ABSTRACT

A biological specimen-containing and/or reagent mixing well used in centrifuge tubes, microtitre plates or trays and the like, and related methods, which comprises shelves or ledges within the specimen well each of which comprises a substantial nonvertical surface component, and functions to receive and temporarily store a desired quantity of reagent against premature delivery ot the bottom region of the well thereby accommodating dispensing of the reagent into the bottom region at precisely the desired and proper point in time.

7 Claims, 1 Drawing Sheet

DISPENSING REAGENTS IN A SPECIMEN WELL

FIELD OF INVENTION

The present invention relates generally to dispensing of reagents, e.g. for the testing of biological specimens, such as blood serum, and more particularly to novel specimen testing and reagent mixing wells comprising structure which temporarily stores a minute quantity of reagent within the well against premature release and either dispenses one or more reagents for delivery to a specimen in the well or dispenses separate reagents to the bottom of the well without a specimen for reagent mixing, each at precisely at an exact point in time.

PRIOR ART

Prior art wells, usually in the form of a centrifuge tube or a microtitre plate or tray, rely solely on surface tension (surface friction) to hold a small droplet of reagent on a vertical or nearly vertical wall above the specimen prior to the time when a plurality of reagents are to be mixed in the absence of a specimen or one or more reagents are to be introduced into a specimen in the bottom of the well to commence biological testing. So placed, surface tension often fails to hold the reagent on the vertical or nearly vertical wall away from the specimen as desired.

When reagent prematurely so breaks the force of surface tension, it prematurely begins to react with other reagents or with the specimen. This leads to erroneous test results. Restated, it is critical that sequencing reactions begin at the exactly desired time. Reliance on surface tension to hold droplets of reagents on the substantially vertical interior side wall of a well does not produce consistently accurate reagent mixing or specimen test results.

BRIEF SUMMARY AND OBJECTS OF THE INVENTION

The present invention overcomes or substantially alleviates the above-mentioned problems and, in brief summary, comprises novel specimen testing and reagent mixing wells, and related methods, which function to receive and temporarily store a small amount of one or more reagents within the well against premature introduction into a specimen in the bottom of the well, or against premature mixing of reagents in the absence of a specimen, and accommodates dispensing of the reagent or reagents to the bottom region of the well at precisely the proper point in time.

With the foregoing in mind, it is a primary object of the present invention to substantially resolve the aforesaid problems, i.e. reliance on surface tension to hold one or more reagents on the interior substantially vertical side wall of a specimen testing and/or reagent mixing well which sometimes results in premature mixing of reagents in the absence of a specimen and/or premature introduction of reagent into the specimen.

Another significant object is the provision of novel specimen and/or reagent mixing well structure, and related methods, which functions to receive and temporarily store a small amount of one or more reagents within the well against premature displacement to the bottom region of the well and dispatches the reagent or reagents to the bottom region of the well at precisely the proper point in time.

A further paramount object is the provision of shelf or ledge structure in a specimen and/or reagent mixing well for securely retaining one or more reagents above the bottom region of the well until the same is released from the shelf or ledge structure at the precise point in time when comingling of reagents and/or reagent introduction into a specimen is desired.

These and other objects and features of the present invention will be apparent from the detailed description taken with reference to the accompanying drawings.

DETAILED DESCRIPTION OF THE ILLUSTRATED EMBODIMENT

Figure 1:
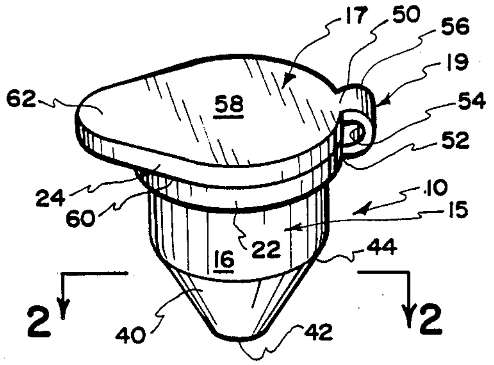
FIG. 1 is a perspective representation of a specimen and reagent mixing container comprising a specimen and reagent mixing well embodying the present reagent-holding invention.

Reference is now made to the drawings, wherein like numerals are used to designate like parts throughout. Specific reference is made to FIGS. 1 and 2 which comprise perspective and cross-sectional representations, respectively, of centrifuge container structure, designated generally 10. Container structure 10 is illustrated as being generally cylindrical in shape. It is to be appreciated that container structure 10 including lid 17 disclosed herein is exemplary. The present invention applies to almost all specimen and reagent mixing containers used in laboratory testing, especially micro specimen containers.

The container structure 10 is illustrated as comprising a small tube or cylindrical container, generally designated 15, a cap or lid, generally designated 17, adapted to close upon the open top of the associated tube 15, and a tether, generally designated 19, by which the associated tube 15 and cap 17 are connected. The entire disposable container structure 10 is preferably formed as one piece from a suitable synthetic resinous material, such as polypropylene or polyethylene, preferably using known single shot injection molding techniques, although some containers within the scope of the present invention can be formed using conventional blow molding techniques.

Each tube 15 comprises a central elongated hollow generally cylindrical wall 16, preferably of uniform thickness throughout. Cylindrical wall 16 integrally merges at its upper end with an annular flange or lip structure comprising an outwardly extending radial enlarged flange or ring 22.

Ring 22 is illustrated as being sized to be radially flush with the exterior annular edge 24 of the associated cap 17. The lip 22 is sized to contiguously receive lid 17 in closed snap-fit relation. This snap-fit union can be manually separated.

The tube 15 is illustrated as comprising a conical bottom 40 terminating in a closed tip 42 at the bottom region thereof. The lower end 40 is generally conically hollow between the annular merger site 44 with wall 16 and the tip 42.

The interior of container structure 10 is preferably formed in such a way that liquid placed to the same level in several identical containers will comprise the same liquid volume.

Also, the length of the cylindrical wall 16 may be shorter and the lower conical end longer, if desired. The internal volume of container structure 10 may vary as necessary or desirable.

A writing surface area may also be provided on the exterior of container structure 10 and/or lid 17. Thus, use of conventional writing instruments allow for easy placement of identifying indicia on the container or lid.

As shown in FIG. 1, cap 17 is joined to cylindrical container 15 by a tether 19. The tether 19 is preferably integrally molded with the associated cap 17 and container 15. The tether 19 is illustrated as being integral with the top region of the cap or lid 17 at site 50 and with the ring 22 of the container at site 52. The tether 19 is illustrated as having a thickness less than one-half of the container lip thickness. The thickness of the tether readily accommodates closing and opening of the lid, yet strong enough to prevent breakage notwithstanding repeated use.

The flat tether 19 is comprised of side edges 54 and 56. It is further comprised of a top surface 58 and a bottom surface 60. When the cap 17 is in the closed position, the strap 19 is folded or looped upon itself, as shown in FIG. 1. On the other hand, when the cap is in the open position, the strap 19 maintains the connection between the cap and container, such that the cap can be positioned in a variety of positions but on no occasion does the cap become separated from the container.

The strap or tether 19 preferably allows maximum efficiency in hinging capabilities. When the cap is closed, the strap 19 is transversely folded along the approximate midpoint thereof, and the major stress placed upon the strap occurs along this location. Therefore, the middle section of the strap may be enlarged in its width or depth to better tolerate the mentioned flexure. The strap is essentially flat, which also accommodates the stated flexure. Thus, the strap provides both a connection and hinging site for the cap 17.

The lid 17 is also illustrated as being of teardrop shape. The tip 62 of the cap 17 extends beyond the lip 22 of the container 15 to allow the user to easily force the lid 17 upward at the tip 62 to open the container. This is accomplished by exerting an upward manual pressure on the cap at the point where the elongated tip 62 extends beyond the ring 22 of the container, thus opening the cap.

Figure 2:
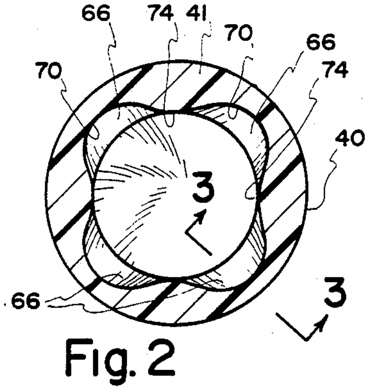
FIG. 2 is a cross-section taken along lines 2—2 of FIG. 1.
Figure 3:
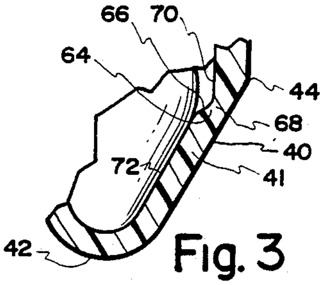
FIG. 3 is a perspective representation of a specimen container comprising a further well embodying the present reagent-holding invention.

As can best be seen from an examination of FIGS. 1–3, the wall 41 of the conical tip 40 is illustrated as being interrupted by four outwardly-directed interiorly disposed shelves or ledges 64. The exterior surface of the conical tip 40 remains without protrusions. Each ledge 64 is illustrated as having a trough-shaped rounded top surface 66. Surface 66 is angular in respect to the vertical and has a substantial horizontal component.

Each shelf 64 is integral within itself and integral with the conical wall 41. Each shelf or ledge 64 is illustrated as having a reduced wall thickness 68. See FIG. 2. Each ledge 64 has a substantially vertical wall surface 70 directly above which is outwardly arcuate in respect to the longitudinal axis of the container 15. Each wall 41 otherwise comprises a sloped interior smooth surface 72. A radially inwardly directed reverse curve surface 74 is interposed and forms a smooth transition between each two adjacent surfaces 70. See FIG. 2. Each wall surface 66 serves as a reagent-receiving shelf or ledge surface upon which one or more droplets of a desired reagent may be placed, using, for example, a micropipette or the like for temporarily storing and preventing each reagent from prematurely reaching the lower portion of the container 15. Thereafter, precisely at the exact moment in time when the reagent on any shelf surface 66 is desired to be comingled with the specimen for testing purposes (such as at the beginning of centrifuging) or reagents are to be mixed in the absence of a specimen, the reagent on any shelf surface 66 is caused to be displaced from the surface 66 into the bottom region of the conical section 40 disposed below the shelf surfaces 66. While the shelf surfaces 66 are illustrated in FIG. 1 as extending outwardly in a radial direction, it is to be appreciated that the shelf surfaces may be non-radial and/or may also be inwardly directed.

FIGS. 1 and 2 illustrate the existence of four shelves providing gently sloped surfaces 66. The exact number of shelves for any particular purpose may be varied to satisfy the number of separate reagents desired to be timely placed at the bottom of the conical well region 42.

Figure 4:
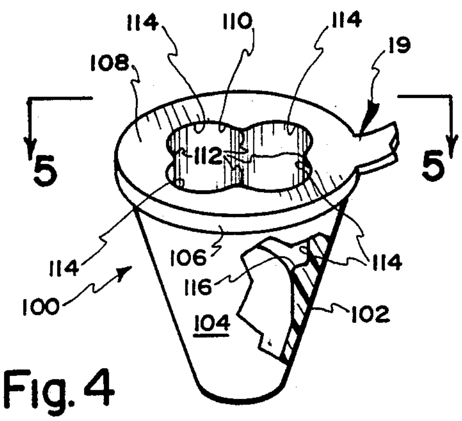
FIG. 4 is a plan view taken along lines 4—4 of FIG. 3.
Figure 5:
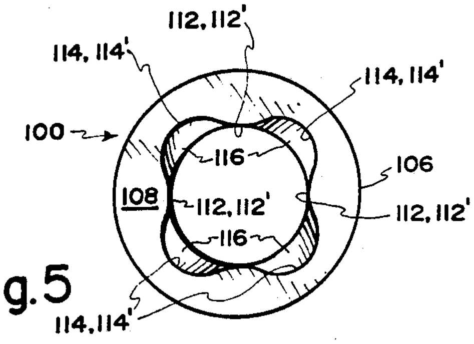
FIG. 5 is a fragmentary plan view of a microtitre plate or tray showing two wells embodying the present reagent-holding invention.

Reference is now made to FIGS. 4 and 5 which illustrate second presently preferred specimen and/or reagent container structure, generally designated 100, fashioned in accordance with the principles of the present invention. Container structure 100 is illustrated as comprising the heretofore described tether 19 for integral attachment of a cap similar to cap 17 to the container structure 100. The cap from the embodiment of FIG. 4 has been removed for purposes of clarity. The container structure 100 comprises a downwardly convergingly tapered container 102, the interior of which is centrally hollow. The exterior surface 104 of the container 102 is illustrated as being smooth without protrusions. The container 102 merges with an upper diametrally enlarged lip 106 which comprises an upper flat generally horizontally-disposed surface 108. Surface 108 is interrupted by an irregular top opening 110, which comprises a series of undulating or reverse curves. The reverse curves of opening 110 comprise seriatum inwardly directed curves 112 and outwardly directed curves 114. The configuration of the opening 110 is continued downwardly into the interior surface of the wall structure adjacent and below the lip 106. These portions of the interior surface of the container structure 100 are identified by the numerals 112′ and 114′.

Each outwardly directed curved wall segment 114′ merges through essentially 90° with a gently sloped rounded trough-shaped shelf surface 116, disposed between two adjacent inwardly directed wall segments 112′. The area of each shelf 116 is sufficient to receive up to several droplets of a desired reagent for temporary storage and prevention of comingling with the specimen prior to the appointed time. Each surface 116 has a substantial horizontal component and a vertical component as well. Each shelf surface 116 provides an anti-gravity resistance to reagent flow prior to the time appointed for displacement, but prior to the time appointed for displacement, but accommodates flow to the bottom of the container below the shelf surface 116 responsive to centrifuging or the like. Thus, the primary reagent retention force provided by the present invention is support counter to gravity, as opposed to only surface tension or surface friction.

Figure 6:
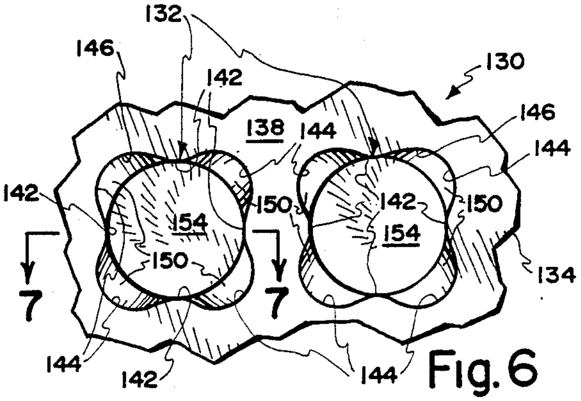
FIG. 6 is a fragmentary cross-section taken along lines 6—6 of FIG. 5.
Figure 7:
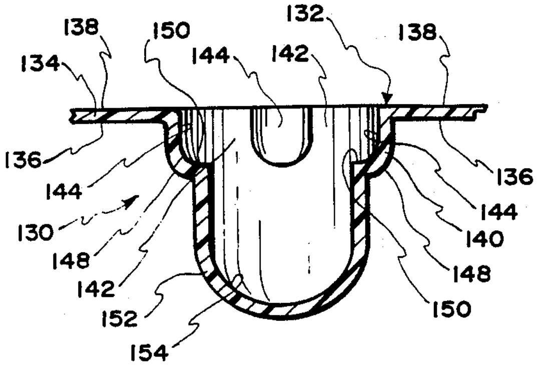

Reference is now made to a third specimen well embodiment, generally designated 130 and illustrated in FIGS. 6 and 7. The embodiment 130 comprises a microtitre plate or tray, which comprises a plurality of specimen and/or reagent mixing wells, each generally designated 132. The plurality of spaced wells 132 are integrally formed, preferably by conventional injection molding techniques using one-shot technology as part of an entire tray 130. Tray 130 comprises an upper flat wall 134 interposed and spanning between the wells 132. Wall 134 is illustrated as comprising a uniform thickness comprising bottom surface 136 and top surface 138. Preferably the tray 130 is formed of transparent polyethylene or polypropylene synthetic resinous material.

Each well 132 is illustrated as comprising an upper lobe-shaped vertically-directed wall 140, illustrated as having a uniform thickness throughout and comprising seriatum radially inwardly directed arcuate wall segments 142 and radially outwardly directed arcuate wall segments 144. The wall segments 142 and 144 are alternately disposed and merge in a reverse curvature configuration. The opening 146 at wall 134 to each specimen well 132 is likewise similarly shaped, i.e. having the same lobe-shaped reverse curve configuration as formed by the heretofore described wall segments 142 and 144.

Each undulating wall segment 144 downwardly merges with an associated, inwardly-directed wall 148, which is illustrated as being of nonuniform thickness. Each wall 148 substantially merges with the adjacent wall segments 142 at their point of minimum radial distance from the center of the well 132. Each wall segment 148 comprises a top rounded trough-shaped surface 150. Each shelf or ledge surface 150 is gently sloped in respect to both the horizontal and the vertical and is located immediately below one of the wall segments 144 between the two immediately adjacent wall segments 142. Each shelf surface 150 is adapted to receive, from a pipette tip or the like, one or more droplets of a desired reagent for anti-gravity temporary storage of the same in such a way that the reagent does not prematurely enter the lower portion of the well 132 at any point in time prior to the precise desired moment.

The wall segments 148 integrally merge with a dome-shaped lower wall 152, which is illustrated as being of uniform thickness throughout and defines, internally at wall surface 154, a bottom site for placement of a biological specimen upon which reagent testing is to occur or for mixing of two or more reagents in the absence of a specimen.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A method of accurately controlling the time of delivery of at least one reagent to the bottom region of a specimen/reagent well to begin an assay incubation period comprising the steps of:

depositing one or more droplets of at least one liquid reagent upon non-wetting, liquid-restraining non-vertical ledge surface means comprising a substantial horizontal component of the specimen/reagent well substantially above the bottom region where a specimen is deposited, for temporary separate storage;

preventing inadvertent displacement of the reagent into the specimen due solely to the force of gravity during temporary storage by adhesion of the liquid reagent to the non-wetting, liquid-restraining non-vertical ledge surface means;

causing entry of the reagent into the bottom region of the well at an exact selected point in time by using other force in addition to gravity to cause the reagent temporarily restrained upon the non-wetting, liquid-restraining non-vertical ledge surface means to flow from the ledge surface means into the bottom region at the point in time when mixing and incubation is to begin;

centrifuging the mixed reagent and specimen.

2. A method according to claim 1 wherein the depositing step comprises placing a plurality of reagents at separate spaced ledge surface means each comprising a substantial horizontal component substantially above the bottom region in the specimen/reagent wall whereby, after each reagent has been placed on its separate ledge surface means, the causing step displaces each reagent from its ledge surface means to the bottom region at substantially the same point in time.

3. A method according to claim 1 wherein the centrifuging step comprises placing the specimen/reagent well with mixed reagents and specimen into a centrifuge machine.

4. A method by which a liquid sample and a liquid reagent are separately deposited and thereafter separately retained at spaced sites in a vessel for later mixing only at a preselected time by physically-induced motion such that a reaction period is accurately created and precisely controlled comprising the steps of:

introducing a liquid sample and at least one liquid reagent through an open top into a vessel;

depositing the liquid sample on a bottom surface of the vessel;

depositing the liquid reagent upon an intermediate non-vertical ledge surface comprising a substantial horizontal component within the vessel above the bottom surface and separate from the liquid sample;

preventing, by reason of the nature and characteristics of non-wetting material of the intermediate non-vertical ledge surface, flow of the liquid reagent from said intermediate non-vertical ledge surface against flow caused by gravity when the vessel is in a static condition;

causing displacement of the vessel by externally applied physically-induced motion at a desired time sufficient to cause the liquid reagent to flow downwardly from the intermediate ledge surface into the liquid sample at a precise predetermined time.

5. A method according to claim 4 wherein the causing step comprises imparting externally applied physical motion to the vessel by a centrifuge machine.

6. A method by which sample and reagents are independently, and separately deposited in a vessel at one time and later mixed at a preselected time by externally-applied force such that a reaction period is accurately created and precisely controlled comprising the steps of:

placing a liquid sample and at least one liquid reagent at spaced surface positions one above the other in a vessel one surface position comprising the bottom of the vessel and the other comprising a ledge surface comprising a substantial horizontal component above the bottom;

statically holding the higher liquid upon the ledge surface against flow due to the force of gravity;

displacing the higher liquid from its surface position by application of external force to the vessel to cause the higher liquid to flow from the ledge surface into the lower liquid and externally agitating the mixed liquids within the vessel.

7. A method according to claim 6 whereby the displacing and agitating steps are caused by centrifuging of the vessel.

* * * * *